United States Patent [19]

Martin et al.

[11] Patent Number: 4,931,393
[45] Date of Patent: Jun. 5, 1990

[54] NON-INFECTIOUS MUTANT CLONE OF HIV

[75] Inventors: Malcolm A. Martin, Bethesda, Md.; Ronald Willey, Alexandria, Va.

[73] Assignee: The United States of America as represented by the Department of Health and Human Services, Washington, D.C.

[21] Appl. No.: 95,837

[22] Filed: Sep. 14, 1987

[51] Int. Cl.$^5$ .................... C12N 7/00; C12N 15/00; C07H 15/12
[52] U.S. Cl. .............................. 435/235; 435/172.3; 435/320; 536/27
[58] Field of Search ................ 435/68, 91, 70, 235, 435/320, 236, 237, 240; 536/27; 935/32, 34, 57

[56] References Cited

U.S. PATENT DOCUMENTS 4,752,565 6/1988 Folks et al. ........................ 435/5

OTHER PUBLICATIONS

Robey et al., (1986) Proc. Nat'l. Acad. Sci. Sci. 7023.
Haln et al., (1984) Natuer 312: 166–9.
Willey etal., 1988, J. Virol. 62: 139–147.
Adachi et al., *Journal of Virology* 59:284–291 (1986).
Karin, et al., *Proc. Natl. Acad. Sci. U.S.A.*, 81:337–341 (1984).
Adachi et al., *Journal of Virology*, 61:209–213 (1987).
Benn, et al., *Science*, 230:949–951 (1985).
Willey et al., *Proc., Natl. Acad. Sci. U.S.A.*, 83:5038–5042 (1986).

*Primary Examiner*—Robin L. Teskin
*Assistant Examiner*—Beth Burrous
*Attorney, Agent, or Firm*—Mishrilal Jain

[57] ABSTRACT

The present invention is related to providing a non-infectious molecular clone of a mutant HIV and HIV proteins useful as immunogens and reagents for diagnostic kit.

2 Claims, No Drawings

NON-INFECTIOUS MUTANT CLONE OF HIV

BACKGROUND OF THE INVENTION

1. Technical Field

The present invention is related generally to human immunodeficiency virus (HIV). More particularly, the present invention is related to providing a non-infectious molecular clone of a mutant HIV and HIV proteins useful as immunogens and reagents for diagnostic kit.

2. State of the Art

The acquired immunodeficiency syndrome (AIDS) is believed to be caused by a retrovirus known as human immunodeficiency virus or HIV. Presently HIV proteins used as antigens in immunochemical screening tests and the like, are derived from tissue culture systems replicating infectious viral particles. Of course, handling of such infectious products is not without risk.

SUMMARY OF THE INVENTION

It is, therefore, an object of the present invention to provide a non-infectious molecularly cloned HIV DNA with a single amino acid mutation in the HIV env gene.

It is another object of the present invention to provide viral proteins produced by the cloned HIV mutant.

It is a still further object of the present invention to provide diagnostic reagents comprising the mutant DNA and/or the proteins produced by the cloned mutant HIV.

It is yet another object of the present invention to provide a pharmaceutical composition comprising HIV proteins derived from the HIV mutant of the present invention capable of inducing neutralizing antibodies in a susceptible host.

Various other objects and advantages of the present invention will become apparent from the Detailed Description of the Invention.

DETAILED DESCRIPTION OF THE INVENTION

The above and various other objects and advantages of the present invention are achieved by providing a non-infectious molecular clone of a mutant HIV DNA and obtaining viral proteins expressed by this clone and employing these proteins as anti-viral agents, diagnostic reagents, or as immunogens for an AIDS vaccine.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Construction of Mutant Molecular Clone

The mutant proviral DNA (pNL4-3/7055) was derived from an infectious plasmid clone of HIV, pNL4-3 (Adachi et al, *Journal of Virology* 59: 284, 1986). A 2.7 kb EcoRI-BamHI restriction fragment containing the amino terminal 2267 nucleotides of the envelope gene was cloned into M13 vectors mp18 and mp19 and specific nucleotide changes introduced using oligonucleotide-directed mutagenesis as described by Zoller et al (DNA 3: 479, 1984). The mutagenic oligonucleotide used to produce clone pNL4-2/7055 was 5-ACTGCTGTTAcAaGGCAGTCTAG-3'. The lower case letters identify nucleotide changes that were introduced. The mutant 2.7 kb EcoRI-BamHI fragment was isolated from the replicative form of M13 DNA and cloned back into EcoRI-BamHI restrictive pNL4-3/7055 following standard techniques well known in the art.

Of course, an advantage of the clone of the present invention is that, for the first time, an unvariable source comprising all molecular components except the mutational site, which can direct the synthesis of a non-infectious HIV now becomes available. By producing various gene segments, either in whole or in part, of the cloned mutant DNA through standard restriction enzyme treatment, and introducing these gene segments into suitable and efficient prokaryotic or eukaryotic expression vectors (such as virus, bacteria, yeast and the like) by standard methodology well known in the art, a variety of gene products (polypeptides) from the mutant clone can now be generated. Distinctive HIV polypeptides (such as capsid) including, of course, the mutant envelope protein thus synthesized by using the viral gene segments from the cloned mutant DNA of the present invention, can then be obtained, isolated, purified, and analyzed (e.g. for amino acid sequencing) following standard methodologies well known to one or ordinary skill in the art, such as Robey et al., *Proc. Natl. Acad. Sci. USA* 83: 7023, 1986.

The mutant DNA and the purified proteins can then be employed either alone or as a pooled admix of proteins for such preparations as anti-viral agents, diagnostic reagents or as immunogens for the AIDS vaccine.

The antigen(s) derived from the clone of the present invention can be administered to a host susceptible to HIV to induce production of protective antibodies against HIV. A vaccine particularly for treating high risk groups of patients, in accordance with the present invention, thus comprises an immunogenic amount of the antigen(s) of the present invention made in a pharmaceutically acceptable vehicle, such as non-toxic buffer, physiological saline and the like.

A deposit of the clone of the present invention has been made at the ATCC, Rockville, Md. on July 12, 1987, under the accession number 67467. This deposit shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. The clone which is deposited at ATCC under accession number 67467.

2. A mutant human immunodeficiency virus produced by mammalian cells infected with the clone of claim 1.

* * * * *